US005989225A

United States Patent [19]

Bodicky et al.

[11] Patent Number: 5,989,225

[45] Date of Patent: Nov. 23, 1999

[54] GASTROINTESTINAL-TYPE TUBE INSERTION OR REMOVAL DEVICE

[75] Inventors: Raymond O. Bodicky, Oakville, Mo.; Peter M. Dyck, Fernandina Beach, Fla.

[73] Assignee: Sherwood Services AG, Schaffhausen, Switzerland

[21] Appl. No.: 08/820,793

[22] Filed: Mar. 19, 1997

Related U.S. Application Data

[60] Provisional application No. 60/013,907, Mar. 19, 1996.

[51] Int. Cl.[6] .......... A61M 7/00

[52] U.S. Cl. .......... 604/174; 604/905; 128/DIG. 26

[58] Field of Search .......... 604/174–180, 604/283, 905, 164, 264; 128/DIG. 26

[56] References Cited

U.S. PATENT DOCUMENTS

| | | | |
|---|---|---|---|
| 3,261,357 | 7/1966 | Roberts et al. | 128/348 |
| 3,794,041 | 2/1974 | Frei et al. | 128/348 |
| 3,814,080 | 6/1974 | Norman | 128/2 |
| 4,735,615 | 4/1988 | Uddo, Jr. et al. | 604/178 |
| 4,944,732 | 7/1990 | Russo | 604/247 |
| 5,007,900 | 4/1991 | Picha et al. | 604/106 |
| 5,007,914 | 4/1991 | Schweigerling | 606/108 |
| 5,176,648 | 1/1993 | Holmes et al. | 604/164 |
| 5,183,464 | 2/1993 | Dubrul et al. | 128/3 |
| 5,234,425 | 8/1993 | Fogarty et al. | 606/1 |
| 5,267,968 | 12/1993 | Russo | 604/174 |
| 5,267,983 | 12/1993 | Oilschlager et al. | 604/283 |
| 5,375,588 | 12/1994 | Yoon | 128/4 |
| 5,391,156 | 2/1995 | Hildwein et al. | 604/174 |
| 5,407,430 | 4/1995 | Peters | 604/104 |
| 5,456,699 | 10/1995 | Armstrong | 606/108 |
| 5,484,420 | 1/1996 | Russo | 604/178 |

*Primary Examiner*—Wynn Wood Coggins
*Assistant Examiner*—Deborah Blyveis
*Attorney, Agent, or Firm*—Mark S. Leonardo; Brown, Rudnick, Freed & Gesmer

[57] ABSTRACT

A gastrointestinal-type tube insertion or removal device includes a body portion, a finger grip portion secured to an end of the body portion, and arm lifts secured to an end of the body portion opposite the finger grip portion. One or more optional stabilizing lifts may likewise be secured to the insertion or removal device in close proximity to the arm lifts. Also methods of using the gastrointestinal-type tube insertion or removal device are described for inserting or removing a skin level gastrointestinal-type tube.

18 Claims, 5 Drawing Sheets

GASTROINTESTINAL-TYPE TUBE INSERTION OR REMOVAL DEVICE

This application claims benefit of Provisional Appl. 60/013,907, filed Mar. 19, 1996.

FIELD OF THE INVENTION

The present invention relates to a device for use with gastrointestinal-type tubes and more particularly to an insertion or removal device for use with gastrostomy-type devices.

BACKGROUND OF THE INVENTION

Low profile gastrointestinal tubes are frequently used for long term tube fed patients who are ambulatory and/or in a combative state and require a smaller, more "manageable" gastrostomy device. These smaller, more manageable devices presently utilize two different types of internal retention bolsters each of which attach to a distal end of the gastrointestinal tube to hold and affix a hollow organ of choice, e.g. the stomach, against the posterior abdominal wall. The hollow organ is so affixed by capturing the organ wall and abdominal wall between an internal retention bolster and an external retention skin disc each of which are attached to opposite ends of a gastrointestinal tube. The gastrointestinal tube is preferably of a short length slightly greater than the combined thicknesses of the abdominal and organ walls. The first type of internal retention bolster of the two types available remains the dominant type on the market and utilizes a deformable obturatable retention bolster to secure the gastrointestinal tube within the organ of choice. The method of using this type of obturatable retention bolster consists of inserting an obturator rod into the lumen of the gastrointestinal tube to abut or engage the distal end of the bolster and mechanically elongate and thereby slenderize the silicone, latex or polyurethane bolster to a size about that of the diameter of the tube. Such slenderization of the bolster allows safe insertion or removal of the tube and bolster into or from an established, matured stoma.

The second type of internal retention bolster utilizes an elastomeric, e.g. silicone, latex, polyurethane, or the like, balloon which is affixed at the distal tip of the gastrointestinal tube. The elastomeric balloon can be inflated and deflated from the proximal, external retention end. The balloon type retention gastrointestinal tubes are often unreliable in nature because the thin membranes of the balloons have a tendency to breakdown if used in a gastric environment. The present invention preferably relates to the first type of low profile gastrostomy device which uses an obturatable retention bolster for affixing the organ of choice.

Obturatable retention bolsters are currently the most common means used to secure low profile skin level gastrointestinal tubes in a matured stoma. However, due to the fact that the tubes are precisely sized to fit the exact depth of the stoma, placement can be both difficult and dangerous. The desirable short length of the skin level gastrointestinal tube makes it very difficult to place. Prior to the present invention, in order to properly place a tube, two fingers had to be placed under the external retention skin disc while pressing the proximal end of the obturator with the thumb. In so doing, the obturator fully obturates and elongates the obturatable retention bolster secured to the distal end of the tube and in communication with the distal end of the obturator. While obturating and elongating the bolster to slenderize the same, the bolster must be pushed into and through the stoma. For proper gastrostomy tube placement, the entire internal retention bolster, obturated to a slenderized configuration, must be completely within an organ such as the stomach prior to deactivating the obturation mechanism. The obturation mechanism is deactivated by withdrawing the obturator to allow the internal retention bolster to assume its preset enlarged shape. However, because the tube length between the distal retention bolster and the external retention skin disc is so closely matched to the thicknesses of the organ and abdominal walls, little extra room remains for manipulation thereof with two or more fingers inserted between the skin and the external skin disc. Thus, a tremendous amount of force must be placed on the tube or catheter and on the patient's abdomen for proper placement. Such a tremendous force is required for placement in order to ensure that the internal retention bolster is completely within the organ prior to deactivating the obturator and allowing the slenderized internal retention bolster to assume its natural enlarged shape.

Since this tube placement procedure is usually performed by "blind" bedside placement without x-ray or endoscopic confirmation, there have been deaths and other serious complications reported where the internal retention bolster was allowed to expand before it was fully within the desired organ. Premature expansion of the retention bolster allows the organ, such as the stomach to separate from the abdomen and in such a case allows nutritional formula, gastric contents and/or air to be delivered into the peritoneum.

The short length of skin level gastrointestinal tubes, which inherently lack space between the internal bolster and the external skin disc for manipulation thereof, has also hindered and sometimes prevented clinicians from using the obturator to re-slenderize the bolster prior to removal of the tube. In such a situation, forceful traction has been utilized to forcefully overcome the resistance of the internal bolster to deform the bolster as it is forced through the stoma to remove the catheter from the patient. Forcefully pulling out a gastrointestinal tube with traction rather than by means of re-obturation with this type of large internal retention bolster is both painful and damaging to the integrity of the matured stoma site.

A method and apparatus that would facilitate obturation of the gastrointestinal-type tube for more reliable insertion and removal thereof would be desirous. Such a device would serve to decrease stress on the stoma, decrease pain experienced by the patient upon removal of the tube, and help prevent leakage of fluids such as stomach acids from around the stoma which result from improper placement of the gastrostomy device upon insertion.

SUMMARY OF THE INVENTION

The present invention provides an insertion or removal tool for use with low profile, skin level devices and standard length higher profile access gastrointestinal-type tubes which provides significant benefits to the user. Specifically, the instant invention provides a safer, more comfortable, reliable proper placement means for inserting or removing access devices such as, but not limited to, gastrointestinal-type tubes providing access to organs, such as but not limited to, the stomach, bladder, gall bladder and other hollow organs. The device of the present invention comprises a body portion, a finger grip portion secured or integrally formed to said body portion, and an arm lift portion secured or integrally formed to extend from said body portion opposite said finger grip portion. Optionally, one or more stabilizing lifts can be secured or integrally formed to said body portion between said finger grip portion and said arm lift portion within close proximity to said arm lift portion.

A preferred embodiment of the apparatus of the present invention comprises a body portion, a finger grip portion secured or integrally formed to an end of said body portion, and a spaced arm lift portion secured or integrally formed to extend perpendicularly from an end of said body portion opposite said finger grip portion. Optionally, one or more stabilizing lifts may be secured or integrally formed approximately perpendicular to said body portion and approximately parallel to said arm lift portion between said finger grip portion and said arm lift portion within close proximity to said arm lift portion.

Another preferred embodiment of the present invention comprises two parallel body portions maintained in a planar parallel state by means of a connecting bar attached or integrally formed perpendicular therebetween, a finger grip portion secured or integrally formed to an end of each of said body portions, spaced parallel arm lifts secured or integrally formed approximately perpendicular to an end of said body portions opposite each said finger grip portions, and one or more optional stabilizing lifts secured or integrally formed approximately perpendicular to said body portions between said finger grip portions and said arm lifts within close proximity to said arm lifts.

The gastrointestinal-type tube insertion or removal device of the preferred embodiments disclosed above may be used to insert a tube by placing the tube's external retention skin disc between said arm lifts and optional stabilizing lifts, or between the finger grip portion and arm lifts if no stabilizing lifts are present. A downward pressure is then applied on said obturator to lock the obturator with one or more teeth members of the subject device to maintain the bolster in a slenderized state. Next, the finger grip portion is advanced in the direction of a stoma until the tube is inserted through the stoma and the tube external retention skin disc rests on the stoma. The obturator is then deactivated by releasing pressure therefrom by unlocking the same from the teeth members to allow the internal retention bolster to expand to its preconfigured shape, Lastly, the device is removed from said tube external retention skin disc.

The gastrointestinal tube insertion or removal device of the present invention may be used to remove a tube by placing said arm lifts below the base of said tube external retention skin disc, activating the obturator by applying a downward pressure thereto in the direction of said stoma to elongate and minimize the size of the internal retention bolster and locking the obturator in this position with one or more teeth members, and applying an upward pressure away from stoma on said finger grip portion until the external retention skin disc and tube are removed from the stoma.

Accordingly, it is a primary objective of the instant invention to provide a means of reliably positioning a gastrointestinal-type tube. It is a further objective to provide an easily manipulatable insertion or removal device for properly positioning a gastrointestinal-type tube.

Other objects, features and advantages of the invention shall become apparent in view of the description when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
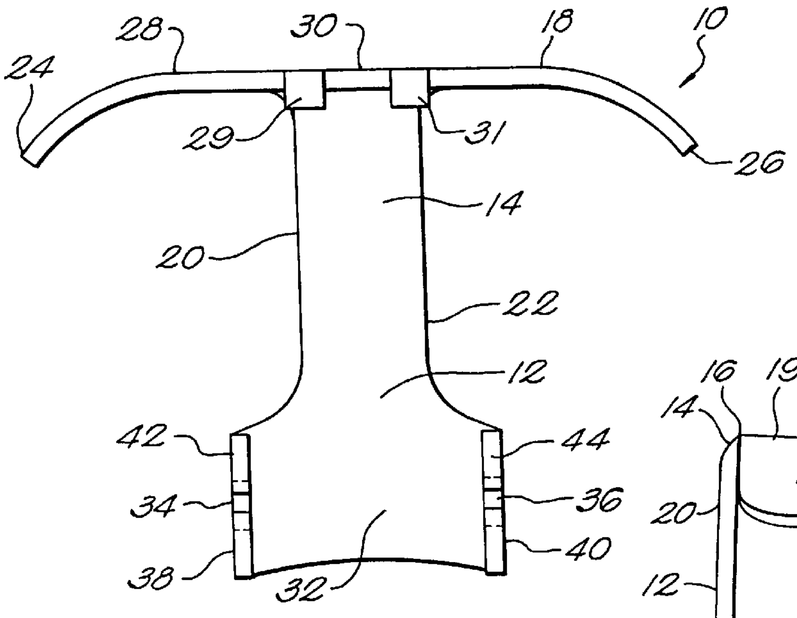
FIG. 1 is a plan view of the gastrointestinal-type tube insertion or removal device of the present invention.
Figure 2:
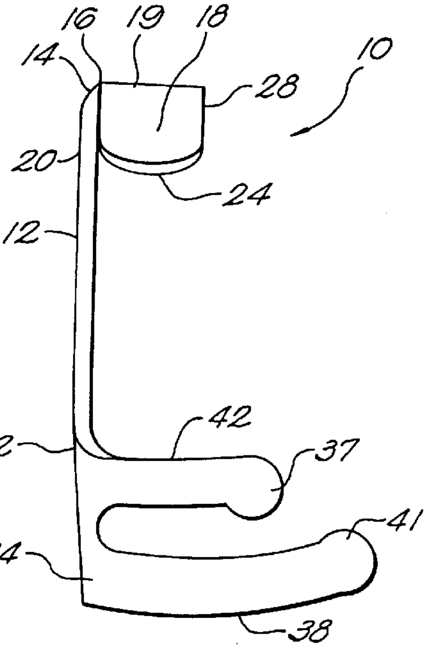
FIG. 2 is a side elevational view of the device of FIG. 1.
Figure 3:
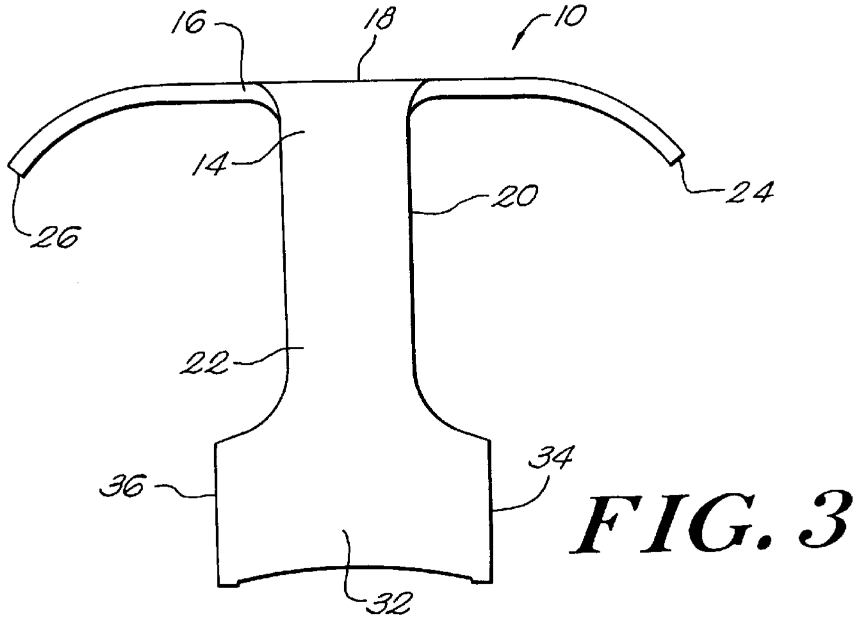
FIG. 3 is a bottom plan view of the device of FIG. 1.
Figure 4:
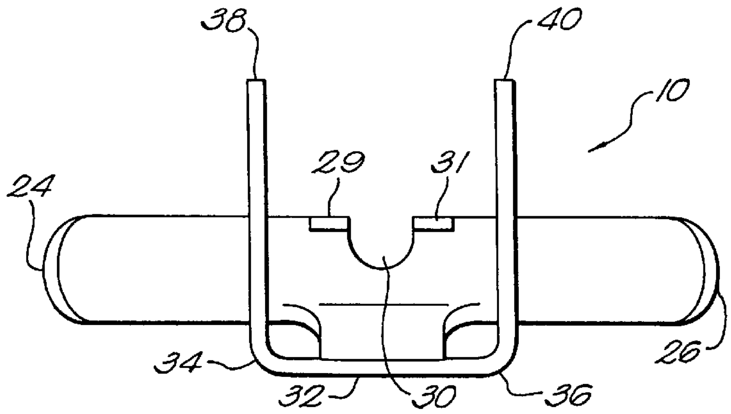
FIG. 4 is an end elevational view of the device of FIG. 1.
Figure 5:
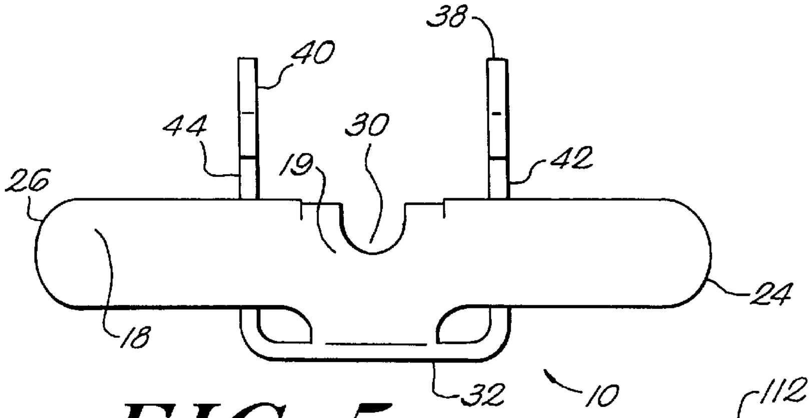
FIG. 5 is an end elevational view of the device of FIG. 1.
Figure 6:
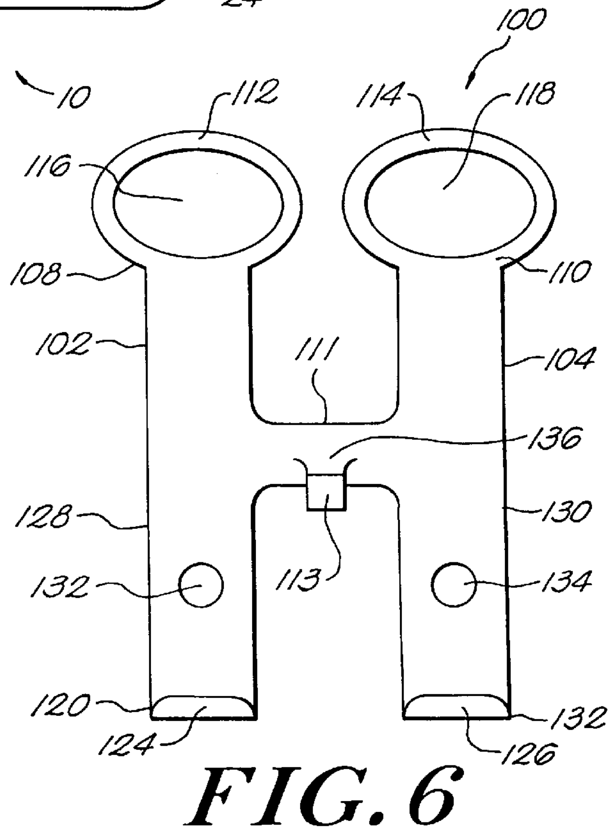
FIG. 6 is a plan view of another embodiment of the gastrointestinal-type tube insertion or removal device of the present invention.
Figure 7:
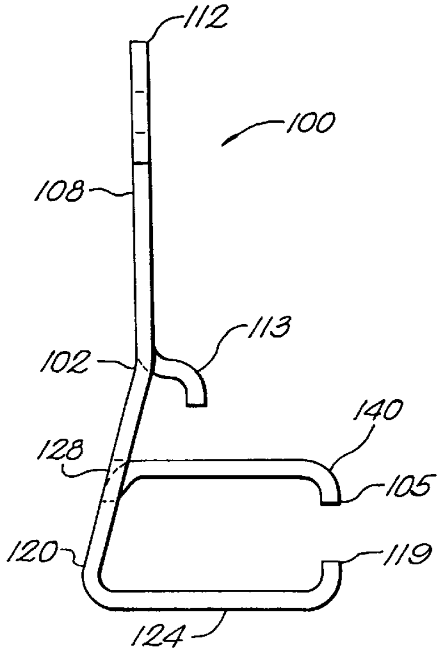
FIG. 7 is a side elevational view of the device of FIG. 6.
Figure 8:
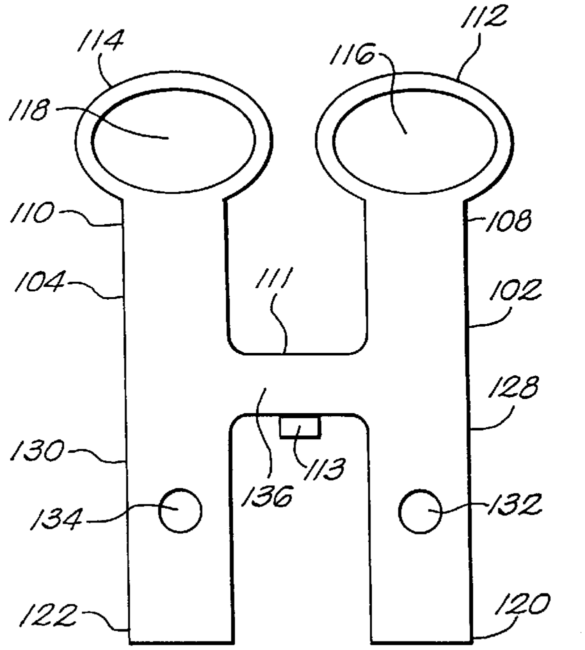
FIG. 8 is a bottom plan view of the device of FIG. 6.
Figure 9:
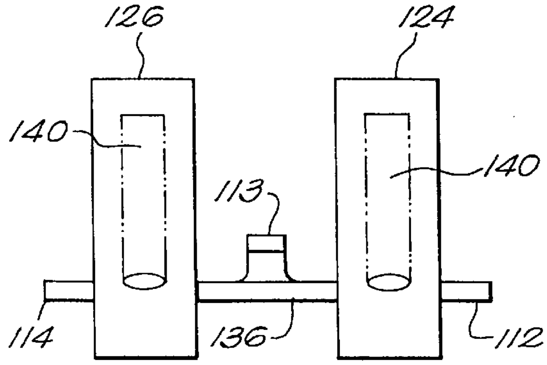
FIG. 9 is an end elevational view of the device of FIG. 6.
Figure 10:
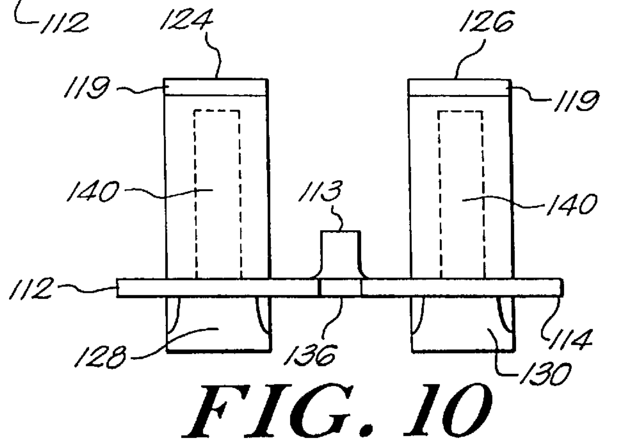
FIG. 10 is an end elevational view of the device of FIG. 6.
Figure 11:
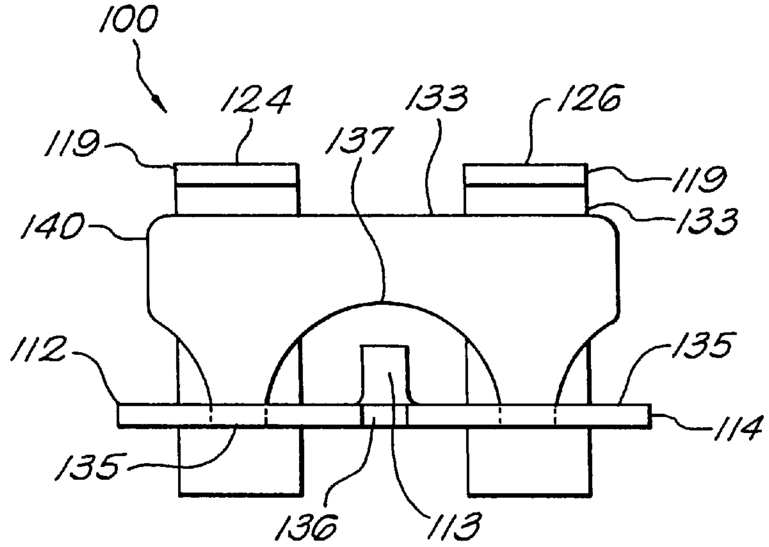
FIG. 11 is a side elevational view of the device of FIG. 6 with optional stabilizing lifts.

Referring to the drawings, a first embodiment of the gastrointestinal-type tube insertion or removal device of the present invention is illustrated and generally indicated as 10 in FIGS. 1–5, 12 and 13, and a second embodiment of the device is illustrated and generally indicated as 100 in FIGS. 6–11 and 14.

Figure 13:
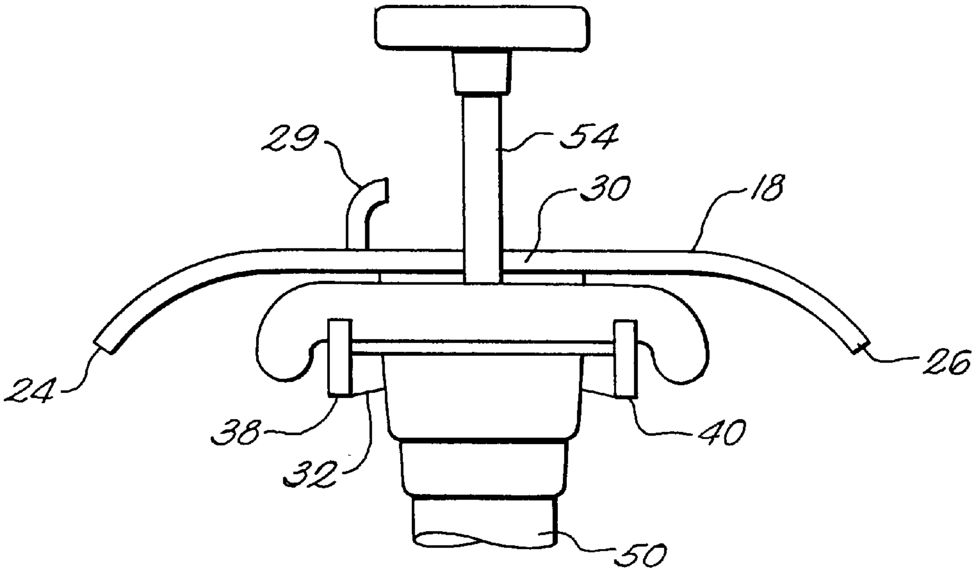
FIG. 13 is an enlarged plan view of a modified embodiment of the gastrointestinal-type tube insertion or removal device of FIG. 1 illustrating the absence of the optional stabilizing lifts, an altered tooth member and the insertion or removal of a gastrointestinal-type tube.

The gastrointestinal tube insertion or removal device 10 comprises a rigid body portion 12 having an upper region 14 permanently secured or integrally formed with the backside portion 16 of a grip portion 18. The grip portion 18 extends outwardly beyond both opposed upper sides 20 and 22 of rigid body portion 12 to form opposed finger grip tips 24 and 26. Opposed finger grip tips 24 and 26 may be flat lying in the same plane as grip portion 18 or may be slightly curved towards rigid body portion 12 for added comfort. Preferably finger grip tips 24 and 26 are curved. Opposite said back side portion 16 of grip portion 18 is front side portion 28. Front side portion 28 lies in a plane parallel or approximately parallel to that of rigid body portion 12. Centered along front side portion 28 is groove 30. Extending downwardly towards rigid body portion 12 on the side of groove 30 are one or more teeth members 29 and 31. Rigid body portion 12 likewise has a lower region 32. Permanently secured or integrally formed with opposed lower sides 34 and 36 of lower region 32 are opposed arm lifts 38 and 40 and optionally stabilizing lifts 42 and 44. FIG. 13 best illustrates a device of the present invention without optional stabilizing lifts 42 and 44. Arm lifts 38 and 40 and optional stabilizing lifts 42 and 44 extend outwardly from lower region 32 at approximately 90° angles therefrom to be approximately perpendicular thereto. Arm lifts 38 and 40 and stabilizing lifts 42 and 44 extend outwardly from lower region 32 in generally a parallel manner. However, arm lifts 38 and 40 may be flat, slightly upwardly curved or slanted toward said stabilizing lifts 42 and 44 and/or have raised ball-like tips 41 thereon. Likewise, stabilizing lifts 42 and 44 may optionally be flat, slightly curved or slanted in a downward direction toward arm lifts 38 and 40 and/or have depending ball-like tips 37 thereon. Preferably, arm lifts 38 and 40 and stabilizing lifts 42 and 44 are approximately parallel and slightly curved with ball-like tips 37 or 41 thereon. Stabilizing lifts 42 and 44 and arm lifts 38 and 40 may be the same length or of differing lengths although preferably arm lifts 38 and 40 extend outwardly from lower region 32 farther than stabilizing lifts 42 and 44. Likewise, lower region 32 may be flat or have a slightly concave-like curve with respect to arm lifts 38 and 40 and stabilizing lifts 42 and 44. Lower region 32 is preferably concavely curved or slightly angled.

Another embodiment of the gastrointestinal-type tube insertion or removal device 100 comprises rigid body portions 102 and 104 permanently secured or integrally formed so as to each be parallel and in the same plane with respect to the other by means of connecting arm 136. Connecting arm 136 lies in the same plane with rigid body portions 102 and 104 but is secured or integrally formed so as to be perpendicular with respect thereto. Extending outwardly in a perpendicular manner from approximately the middle 111 of said connecting arm 136 is one or more, but preferably one, hooked tooth member 113. Permanently attached or integrally formed to end regions 108 and 110 of rigid body portions 102 and 104 respectively are finger grip portions 112 and 114. Finger grip portions 112 and 114 are formed so as to have apertures 116 and 118 therein. Preferably apperatures 116 and 118 are large enough to accommodate at least one finger in each. Optionally, one or more hooked tooth members 113 may extend in the same plane as connecting arm 136 from one or both finger grip portions 112 and 114 so as to be located therebetween. (See FIG. 14). Opposite end regions 108 and 110 on rigid body portions 102 and 104 are bottom ends 120 and 122. Extending outwardly from bottom ends 120 and 122 perpendicular or approximately perpendicular thereto are arm lifts 124 and 126. Arm lifts 124 and 126 may be flat, slightly curved or slanted toward said finger grip portions 112 and 114 and/or have raised tips 119 thereon. Preferably arm lifts 124 and 126 are slightly curved with tips 119 thereon. On said rigid body portions 102 and 104 in lower regions 128 and 130 between connecting arm 136 and bottom ends 120 and 122 are lift apertures 132 and 134. Lift apertures 132 and 134 allow for the addition of one or more optional stabilizing lifts 140, which extend outwardly approximately parallel to said arm lifts 124 and 126. Should there be only one stabilizing lift 140, a groove 137 is located in attached end 135 opposite free end 133 (See FIG. 11). Optional stabilizing lifts 140 may be attached through lift apertures 132 and 134 by any conventional method such as but not limited to male and female threaded means, friction fit, suitable adhesives or the like, but preferably friction fit. Stabilizing lifts 140 may be flat, slightly curved or slanted toward arm lifts 124 and 126 and/or have depending tips 105 thereon, but preferably slightly curved with tips 105 in the direction of arm lifts 124 and 126. Stabilizing lifts 140 may likewise be of the same length as arm lifts 124 and 126 or of differing lengths but preferably of a shorter or of lesser length than that of arm lifts 124 and 126. Rigid body portions 102 and 104 within the lower regions 128 and 130 between said connecting arm 136 and bottom ends 120 and 122 may be flat or concavely curved or slanted with respect to arm lifts 124 and 126 and optional stabilizing lifts 140. Preferably lower regions 128 and 130 are slightly concave, slanted or angled with respect to arm lifts 124 and 126 and optional stabilizing lifts 140.

Both of the above described embodiments, i.e., 10 and 100, of the present gastrointestinal-type tube insertion or removal device are used to insert or remove gastrointestinal-type tubes. Illustrated best in FIG. 12, device 10 is exemplified although device 100 is used in a like manner, gastrointestinal-type tube 50 is inserted using the present invention by placing the external retention skin disc 56 of a gastrointestinal-type tube between the stabilizing lifts 42 and 44 and the arm lifts 38 and 40 so as to allow the remainder of the tube to extend below said arm lifts 38 and 40. In so manipulating and utilizing the device, the user's index and middle fingers are cupped beneath the finger grip portion 18 and the user's thumb is placed on the exterior surface 19 of the finger grip portion 18 and obturator 54 while locked by one or more teeth members 29 and 31. If optional stabilizing lifts 42 and 44 are not present as illustrated in FIG. 13, the external retention skin disc 56 is placed between the arm lifts 38 and 40 and finger grip portion 18 such that the arm lifts 38 and 40 underlyingly support the skin disk 56. The tube 50 is fed into the peritoneal cavity and into an organ 59 such as the stomach through a stoma 52. The external retention skin disc 56 is placed on the stoma 52 so as to be at skin level and is maintained at this level by applying appropriate force on the gastrointestinal insertion or removal device 10 of the present invention. An obturator device 54 is then used to enlarge the slenderized internal retention bolster 58 to thus hold tube 50 in position. Such enlargement of the slenderized retention bolster is achieved by releasing the obturator device 54 from beneath teeth members 29 and 31 with one's thumb thus releasing the pressure thereon. By releasing the pressure, obturator device 54 extends upwardly from enlarged bolster 58 through groove 30. Groove 30 of device 10 allows the necessary space for manipulating and utilizing the obturator device 54. Once the internal retention bolster 58 has been enlarged, the external retention skin disc 56 is removed from between the stabilizing lifts 42 and 44 if present and arm lifts 38 and 40 by sliding and/or tilting the device away therefrom.

Figure 12:
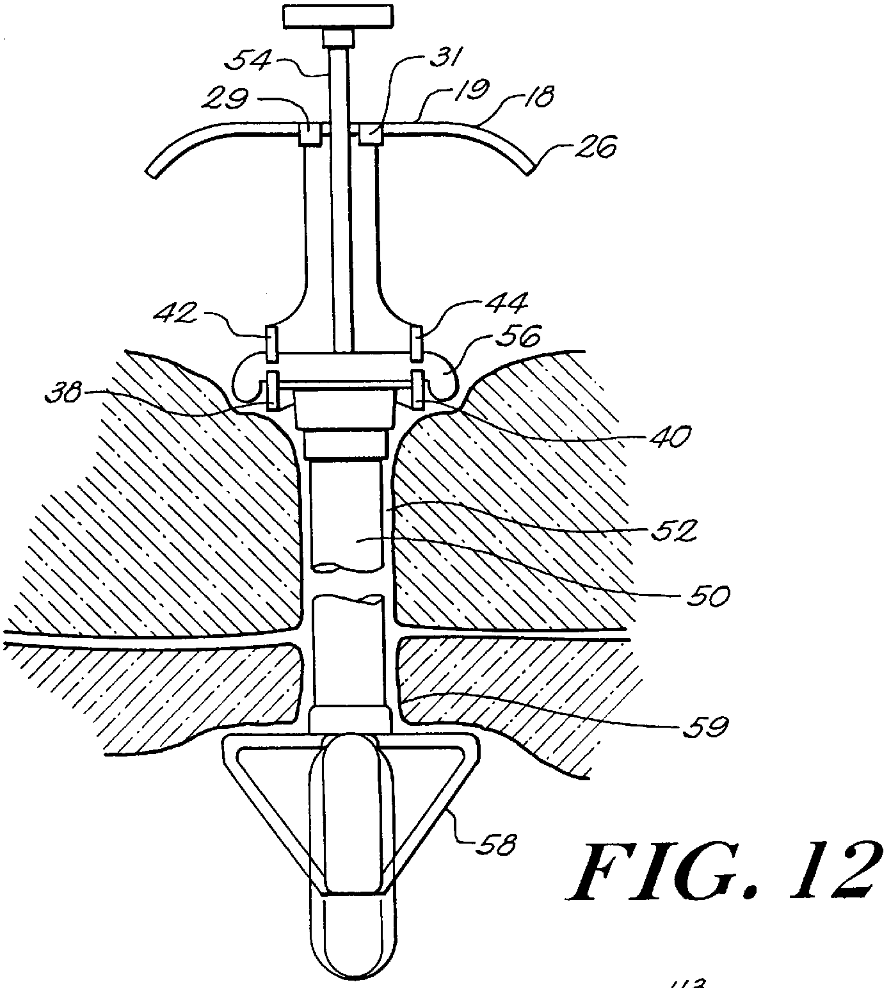
FIG. 12 is an enlarged plan view of the device of FIG. 1 illustrating insertion or removal of a gastrointestinal-type tube.
Figure 14:
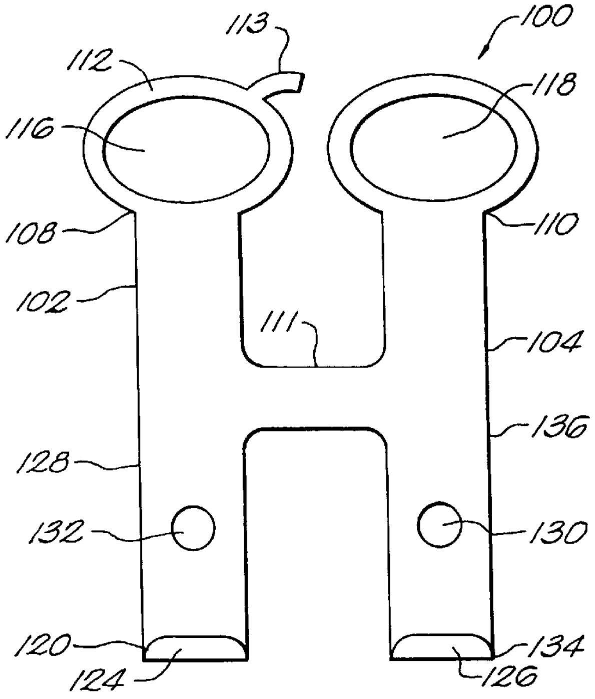
FIG. 14 is an enlarged plan view of the gastrointestinal-type tube insertion or removal device of FIG. 6 illustrating the tooth member on the finger grip portion.

A gastrointestinal-type tube is removed using the present device by reversing the above procedure. Namely, as illustrated in FIG. 12, device 10 is slid and/or tilted so as to locate the external retention skin disc 56 between stabilizing lifts 42 and 44 and arm lifts 38 and 40. Stabilizing lifts 42 and 44 are optional for this procedure. The obturator device 54 is then used to slenderize the internal retention bolster 58. Slenderization is achieved by applying downward pressure toward said stoma on the obturator device 54 with one's thumb to slide the obturator device 54 through groove 30. The obturator device is then locked in this position by means of teeth members 29 and 31 wherein the obturator 54 forces the bolster 58 into an elongated form having a diameter similar to that of the tube. Two teeth members 29 and 31 are preferred although one or more could be utilized. Device 10 is then pulled in a direction away from stoma 52 by having the index and middle fingers cupped beneath the grip portion 18 thus extracting the external retention skin disc 56, attached tube 50 and bolster 58 from the stoma and peritoneal cavity.

The gastrointestinal tube insertion or removal device of the present invention may be made of one or more suitable materials selected from but not limited to the group consisting of metal, synthetic monomers, synthetic polymers, synthetic copolymers and synthetic polymer blends. Preferably the device is integrally formed from metal. If the device is not integrally formed as preferred, the various features of the device may be attached or secured through any suitable means such as but not limited to one or more welds, friction fit, one or more adhesives, male and female threaded means, male and female interlocking means or any combination thereof.

The gastrointestinal tube insertion or removal device of the present invention may be manufactured according to any suitable dimensions but preferably the arm lifts are spaced apart by approximately one half inch to approximately one inch. The optional stabilizing lifts should preferably be spaced apart from the aim lifts by approximately one sixteenth of an inch to one inch. If the optional stabilizing lifts are not present, the finger grip portion may be spaced apart from the arm lifts by approximately one sixteenth of an inch to one inch as illustrated in FIG. 13.

It is seen therefore that the present invention provides an effective gastrointestinal tube insertion or removal device which has specific advantages over the heretofore known means of insertion and removal of gastrointestinal tubes. The device eliminates risks associated with the internal retention bolster being expanded intra-peritoneal before fully inserted in the desired location, allows for reliable positioning of the gastrointestinal-type tube, allows for re-slenderization of the internal retention bolster before removal, provides more comfort for the patient by eliminating the need to apply abdominal pressure for placement and prevents enlargement of the stoma and problems related thereto. Hence, for these reasons as well as others some of which hereinabove set forth, it is seen that the invention represents a significant advancement which has substantial medical and commercial significance.

While there is shown and described herein certain specific embodiments of the invention, it will be manifest to those skilled in the art that various modifications may be made without departing from the spirit and scope of the underlying inventive concept and that the same is not limited to the particular forms herein shown and described except insofar as indicated by the scope of the appended claims.

What is claimed is:

1. A gastrointestinal-type tube insertion or removal device comprising a body portion, a finger grip portion secured to said body portion, and arm lifts secured substantially to an end of said body portion opposite said finger grip portion; wherein, in use, said arm lifts are operable to underlyingly support a skin disk of a gastrointestinal-type tube.

2. The gastrointestinal-type tube insertion or removal device of claim 1 wherein one or more optional stabilizing lifts are secured to said body portion between said finger grip portion and said arm lifts.

3. The gastrointestinal-type tube insertion or removal device of claim 1, wherein said finger grip portion allows for use thereof with an obturator by means of a groove therein.

4. The gastrointestinal-type tube insertion or removal device of claim 1, wherein said finger grip portion allows for the locking of an obturator by means of teeth members extending therefrom.

5. The gastrointestinal-type tube insertion or removal device of claim 1, wherein said device is integrally formed from a suitable material or materials selected from the group consisting of metal, synthetic polymers, and synthetic monomers.

6. The gastrointestinal-type tube insertion or removal device of claim 1, wherein said arm lifts are flat, slightly curved, slanted or have portions raised toward said finger grip portion.

7. The gastrointestinal-type tube insertion or removal device of claim 1, wherein said arm lifts have portions raised toward said finger grip portion.

8. The gastrointestinal-type tube insertion or removal device of claim 1, wherein said one or more stabilizing lifts are secured to said body portion between said finger grip portion and said arm lifts and have portions depending therefrom toward said arm lifts.

9. The gastrointestinal-type tube insertion or removal device of claim 1, wherein said one or more stabilizing lifts are secured to said body portion between said finger grip portion and said arm lifts and are flat, slightly curved, slanted or have portions depending therefrom toward said arm lifts.

10. The gastrointestinal-type tube insertion or removal device of claim 1, wherein said one or more optional stabilizing lifts are secured to said body portion between said finger grip portion and said arm lifts and integrally formed with said device.

11. The gastrointestinal-type tube insertion or removal device of claim 1 wherein said one or more stabilizing lifts are secured to said body portion between said finger grip portion and said arm lifts by means of male and female threaded means, male and female interlocking means, friction fit, one or more suitable adhesives or one or more welds.

12. A method of using the gastrointestinal-type tube insertion or removal device of claim 1 to insert a tube comprising:

placing a tube external retention skin disc portion of a gastrointestinal-type tube between said arm lifts and finger grip portion or stabilizing lifts which are secured to said body portion between said finger grip portion and said arm lifts;

applying downward pressure toward a stoma on said finger grip portion until said tube is inserted through the stoma and the tube external retention skin disc rests in the stoma;

deactivating an obturator extending through said tube to expand an internal retention bolster; and removing said device from said tube external retention skin disc.

13. A method of using the gastrointestinal-type tube insertion or removal device of claim 1 to insert a tube comprising:

placing a tube external retention skin disc portion of a gastrointestinal-type tube between said arm lifts and finger grip portion or stabilizing lifts which are secured to said body portion between said finger grip portion and said arm lifts;

applying downward pressure toward a stoma on said finger grip portion until said tube is inserted through said stoma and said tube external retention skin disc rests in said stoma;

deactivating an obturator extending through said tube to expand an internal retention bolster; and removing said device from said tube external retention skin disc;

wherein said obturator is deactivated and said internal retention bolster is expanded by releasing pressure from said obturator.

14. A method of using the gastrointestinal-type tube insertion or removal device of claim 1 to insert a tube comprising:

placing a tube external retention skin disc portion of a gastrointestinal-type tube between said arm lifts and finger grip portion or stabilizing lifts which are secured to said body portion between said finger grip portion and said arm lifts;

applying downward pressure toward a stoma on said finger grip portion until said tube is inserted through said stoma and said tube external retention skin disc rests in said stoma;

deactivating an obturator extending through said tube to expand an internal retention bolster; and removing said device from said tube external retention skin disc;

wherein said obturator is deactivated and said internal retention bolster is expanded by releasing pressure from said obturator by releasing said obturator from one or more teeth members extending from said finger grip portion.

15. A method of using the gastrointestinal-type tube insertion or removal device of claim 1 to remove a tube comprising:

placing said arm lifts below a tube external retention skin disc portion of a gastrointestinal-type tube;

activating an obturator extending through said tube to slenderize an internal retention bolster attached to said tube; and applying upward pressure away from a stoma on said finger grip portion until said external retention skin disc, tube and internal retention bolster are removed from said stoma.

16. A method of using the gastrointestinal-type tube insertion or removal device of claim 1 to remove a tube comprising:

placing said arm lifts below said tube external retention skin disc;

activating an obturator extending through said tube to slenderize an internal retention bolster attached to said tube; and applying upward pressure away from a stoma on said finger grip portion until said external retention skin disc, tube and internal retention bolster are removed from said stoma;

wherein said obturator is activated and said internal retention bolster is slenderized by applying a downward pressure toward said stoma on said obturator.

17. A method of using the gastrointestinal-type tube insertion or removal device of claim 1 to remove a tube comprising:

placing said arm lifts below a tube external retention skin disc portion of a gastrointestinal-type tube;

activating an obturator extending through said tube to slenderize an internal retention bolster attached to said tube; and applying upward pressure away from a stoma on said finger grip portion until said external retention skin disc, tube and internal retention bolster are removed from said stoma;

wherein said obturator is activated and said internal retention bolster is slenderized by applying a downward pressure toward said stoma on said obturator and locking said obturator beneath one or more teeth members extending from said finger grip portion.

18. The gastrointestinal-type tube insertion or removal device of claim 1 wherein said device is manipulated by cupping one's index and middle finger beneath said finger grip portion and placing one's thumb on said finger grip portion and an obturator portion of a gastrointestinal-type tube.

* * * * *

UNITED STATES PATENT AND TRADEMARK OFFICE

CERTIFICATE OF CORRECTION

PATENT NO. : 5,989,225

DATED : November 23, 1999

INVENTOR(S) : Raymond O. Bodicky, Peter M. Dyck

It is certified that error appears in the above-identified patent and that said Letters Patent is hereby corrected as shown below:

At Column 5, line 23:

The word, "apperatures" should be changed to --apertures--.

Signed and Sealed this

Twenty-eighth Day of November, 2000

*Attest:*

Q. TODD DICKINSON

*Attesting Officer* *Director of Patents and Trademarks*